(12) United States Patent
Ohmiya (10) Patent No.: US 9,903,863 B2
(45) Date of Patent: Feb. 27, 2018

(54) METHOD FOR ANALYZING, SAMPLE ANALYSIS TOOL, METHOD FOR PREVENTING FLOW OF SAMPLE SOLUTION IN UNDESIRED DIRECTION, AND METHOD FOR PREVENTING INCREASE IN BACKGROUND

(75) Inventor: Kazuhiro Ohmiya, Kyoto (JP)

(73) Assignee: Arkray, Inc., Kyoto (JP)

( * ) Notice: Subject to any disclaimer, the term of this patent is extended or adjusted under 35 U.S.C. 154(b) by 1870 days.

(21) Appl. No.: 13/263,725

(22) PCT Filed: Apr. 5, 2010

(86) PCT No.: PCT/JP2010/056186
§ 371 (c)(1),
(2), (4) Date: Oct. 7, 2011

(87) PCT Pub. No.: WO2010/116978
PCT Pub. Date: Oct. 14, 2010

(65) Prior Publication Data
US 2012/0031206 A1  Feb. 9, 2012

(30) Foreign Application Priority Data

Apr. 9, 2009 (JP) ................................. 2009-094835

(51) Int. Cl.
*G01N 33/558* (2006.01)
(52) U.S. Cl.
CPC .................. *G01N 33/558* (2013.01)
(58) Field of Classification Search
USPC .................... 436/518, 810; 435/7.1
See application file for complete search history.

(56) References Cited

U.S. PATENT DOCUMENTS 4,981,786 A * 1/1991 Dafforn .............. G01N 33/5302
422/412
2002/0045278 A1  4/2002 Saruta et al.
(Continued)

FOREIGN PATENT DOCUMENTS

CN    1833169 A    9/2006
CN    1934133 A    3/2007
(Continued)

OTHER PUBLICATIONS

Extended European Search Report dated Feb. 13, 2013 for corresponding European Application No. 10761677.3.
(Continued)

*Primary Examiner* — Melanie Yu Brown
(74) *Attorney, Agent, or Firm* — Knobbe, Martens, Olson & Bear, LLP (57) ABSTRACT

Provided is an analysis method in which increase in a background can be prevented in a simple manner without cost. The analysis method of the present invention is carried out using a sample analysis tool 10 including a development member 11 in which a developing solution supply portion 12, a sample supply portion 13, and a detection portion 14 in which a substance 17 that specifically binds to an analyte 16 in a sample is immobilized are provided in this order from upstream to downstream along the flow of a developing solution. A sample solution is supplied to the sample supply portion 13, and a developing solution is supplied to the developing solution supply portion 12 simultaneously with the supply of the sample solution or prior to the supply of the sample solution. By the development of the developing solution in the development member 11 in the presence of a labeled specifically binding substance 15, the sample solution is introduced to the detection portion 14. In the detection portion 14, a complex 18 of the immobilized specifically binding substance 17, the analyte 16, and the (Continued)

labeled specifically binding substance 15 is formed. The analyte 16 is analyzed by detecting a label 19 in the complex 18.

6 Claims, 5 Drawing Sheets

(56) References Cited

U.S. PATENT DOCUMENTS

| | | | |
|---|---|---|---|
| 2002/0173050 A1* | 11/2002 | DiNello et al. | 436/518 |
| 2003/0040106 A1 | 2/2003 | Hashimoto et al. | |
| 2003/0124618 A1* | 7/2003 | Chen et al. | 435/7.1 |
| 2006/0166374 A1* | 7/2006 | Hubscher | G01N 33/558 436/514 |
| 2007/0031286 A1 | 2/2007 | Mike et al. | |
| 2007/0141717 A1* | 6/2007 | Carpenter | G01N 33/58 436/172 |
| 2008/0193953 A1* | 8/2008 | Takizawa et al. | 435/7.72 |
| 2009/0053829 A1* | 2/2009 | Okamura et al. | 436/501 |
| 2009/0087926 A1* | 4/2009 | Hasegawa et al. | 436/518 |

FOREIGN PATENT DOCUMENTS

| | | | | |
|---|---|---|---|---|
| EP | 0512390 | A1 | 11/1992 | |
| EP | 1329717 | A1 | 7/2003 | |
| EP | 1662257 | A1 | 5/2006 | |
| EP | 1992950 | A1 * | 11/2008 | G01N 33/543 |
| JP | H05-126832 | | 5/1993 | |
| JP | H10-177028 | | 6/1998 | |
| JP | H11-153600 | | 6/1999 | |
| JP | 3248436 | B2 | 1/2002 | |
| JP | 2002-202310 | | 7/2002 | |
| JP | 2005-331463 | | 12/2005 | |
| JP | 3859027 | B2 | 9/2006 | |
| JP | 2007-248073 | | 9/2007 | |
| JP | 2007-322310 | | 12/2007 | |
| JP | 2008-116235 | | 5/2008 | |
| WO | 99/36776 | A1 | 7/1999 | |
| WO | WO 2005/015217 | A1 | 2/2005 | |

OTHER PUBLICATIONS

PCT International Search Report in PCT Application No. PCT/JP2010/056186 dated May 11, 2010 in 2 pages.

Office Action dated Oct. 1, 2013 in corresponding European application No. 10761677.3.

Office Action of the Corresponding Chinese Application (No. 201080016332.9) dated Jul. 26, 2013.

* cited by examiner

ND FOR PREVENTING
METHOD FOR ANALYZING, SAMPLE ANALYSIS TOOL, METHOD FOR PREVENTING FLOW OF SAMPLE SOLUTION IN UNDESIRED DIRECTION, AND METHOD FOR PREVENTING INCREASE IN BACKGROUND

TECHNICAL FIELD

The present invention relates to a method for analyzing (analysis method), a sample analysis tool, a method for preventing a flow of a sample solution in an undesired direction, and a method for preventing an increase in a background.

BACKGROUND ART

Heretofore, for example, in the diagnosis or the like of infectious diseases, sample analysis tools for detecting antigens of pathogens such as bacteria and viruses utilizing an immunoreaction are in widespread use. In such sample analysis tools, immunochromatography (an immunoassay method) is used widely. The immunoassay method is one technique for conducting analysis using substances that specifically bind to an analyte such as the above-described antigen (specifically binding substances). According to the immunoassay method, it is possible to conduct analysis easily and rapidly. In recent years, an immunoassay method in which an enzyme is used as a label (an enzyme immunoassay method) has been developed (see Patent Document 1, for example).

Figure 6A:
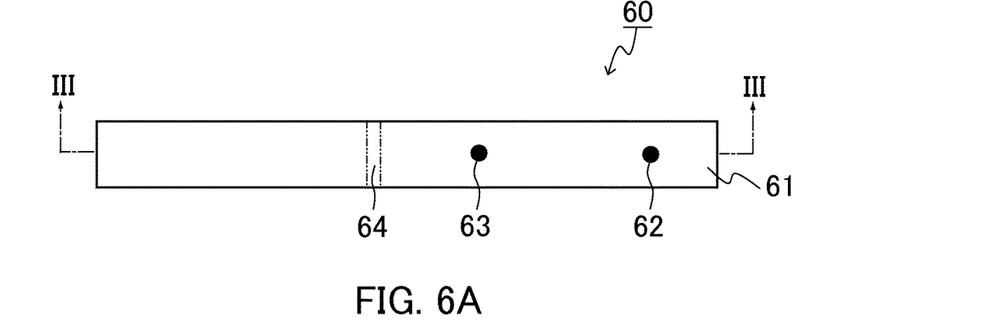
FIG. 6A is a plan view showing an example of the configuration of a sample analysis tool used in a conventional enzyme immunoassay method.
Figure 6B:
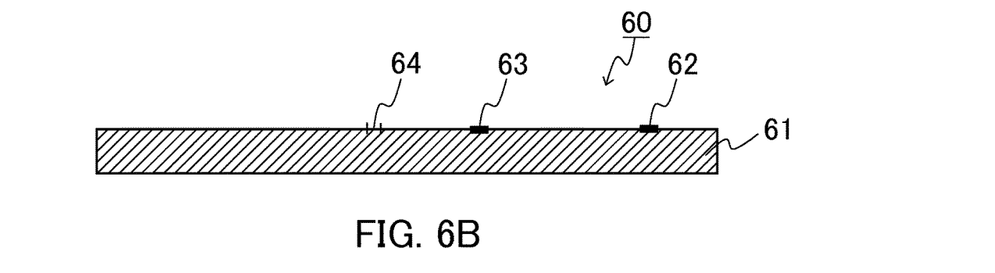
FIG. 6B is a sectional view showing the sample analysis tool, viewed along arrows in FIG. 6A.

The enzyme immunoassay method is carried out in the following manner, for example. Specifically, first, a sample is collected from a nasal cavity or the like, and a sample solution containing the sample is prepared. On the other hand, a sample analysis tool is provided. FIGS. 6A and 6B show an example of the sample analysis tool. FIG. 6A is a plan view of the sample analysis tool. FIG. 6B is a sectional view of the sample analysis tool, viewed along arrows III-III in FIG. 6A. In FIGS. 6A and 6B, common components and portions are given the same reference numerals. In the sample analysis tool 60, a developing solution supply portion 62, a sample supply portion 63, and a detection portion 64 are provided in a porous development member 61 in this order from upstream to downstream along the flow of a developing solution (from the right to the left in FIGS. 6A and 6B). In the detection portion 64, an antibody is immobilized (immobilized antibody).

Figure 6C:
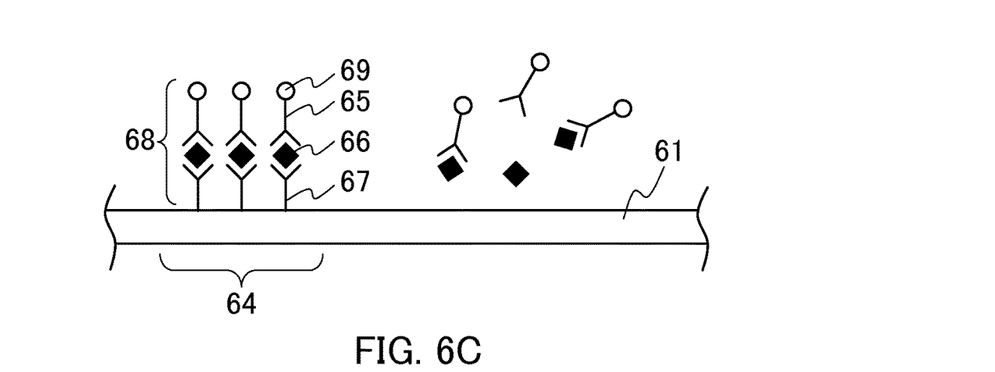
FIG. 6C is a schematic view for illustrating the detection of an antigen in a detection portion.

First, the sample solution is supplied to the sample supply portion 63. Next, a developing solution is supplied to the developing solution supply portion 62. By the development of the supplied developing solution in the development member 61 in the presence of a labeled antibody labeled with an enzyme (an enzyme-labeled antibody), the supplied sample solution is introduced into the detection portion 64. Furthermore, by the development of the supplied developing solution, a substrate is introduced into the detection portion 64 from the developing solution supply portion 62 via the sample supply portion 63. FIG. 6C is a schematic view showing an example of the detection of an antigen in the detection portion 64. In FIG. 6C, the same components and portions as those in FIGS. 6A and 6B are given the same reference numerals. As shown in FIG. 6C, when an antigen 66 as an analyte is present in the sample, a complex 68 of the enzyme-labeled antibody 65, the antigen 66, and the immobilized antibody 67 is formed in the detection portion 64. In this state, by detecting the color development, light emission, or the like caused by the reaction of the enzyme 69 of the enzyme-labeled antibody 65 in the complex 68 with the substrate, the antigen 66 is detected.

CITATION LIST

Patent Document(s)

Patent Document 1: Japanese Patent No. 3248436

BRIEF SUMMARY OF THE INVENTION

Problem to be Solved by the Invention

Immunoassay methods such as the enzyme immunoassay method have a problem of decrease in detection sensitivity due to the increase in a background. In particular, the increase in a background becomes significant when the amount of a sample solution is increased. The increase in a background can be prevented by, for example, using a sample solution holding member, increasing the size of the development member, or the like. Such solutions to the problem, however, require cost. The above-described problems are not specific to the immunoassay methods utilizing an immunoreaction caused by using antibodies that specifically bind to an antigen as an analyte contained in a sample. These problems may occur generally in any analysis method in which substances that specifically bind to an analyte contained in a sample (specifically binding substances) are used.

With the foregoing in mind, it is an object of the present invention to provide an analysis method in which increase in a background can prevented in a simple manner without cost, a sample analysis tool, a method for preventing a flow of a sample solution in an undesired direction, and a method for preventing an increase in a background.

Means for Solving Problem

In order to achieve the above object, the analysis method of the present invention is a method for analyzing a sample containing an analyte using a sample analysis tool. The sample analysis tool includes a development member including a developing solution supply portion, a sample supply portion, and a detection portion provided in this order from upstream to downstream along a flow of a developing solution, wherein a substance that specifically binds to the analyte in a sample is immobilized in the detection portion. The analysis method includes the steps of: supplying a sample solution containing the sample to the sample supply portion; supplying a developing solution to the developing solution supply portion simultaneously with the supply of the sample solution or prior to the supply of the sample solution; and analyzing the analyte by detecting a label in a complex. In the method, the sample solution is introduced to the detection portion by development of the developing solution in the development member in the presence of a labeled substance that specifically binds to the analyte. In the method, the complex containing the immobilized substance that specifically binds to the analyte, the analyte, and the labeled substance is formed in the detection portion.

Furthermore, the sample analysis tool of the present invention is a sample analysis tool for use in the analysis method according to the present invention. The sample analysis tool includes a development member on which a developing solution supply portion, a sample supply portion, and a detection portion are provided in this order from upstream to downstream along a flow of a developing solution. In the sample analysis tool, a substance that specifically binds to an analyte in a sample is immobilized in the detection portion.

Still further, the method for preventing a flow of a sample solution in an undesired direction according to the present invention is a method for preventing a flow of a sample solution in an undesired direction in a sample analysis tool. The sample analysis tool includes a development member including a developing solution supply portion and a sample supply portion provided in this order from upstream to downstream along a flow of a developing solution. The method includes the steps of: supplying a sample solution containing a sample to the sample supply portion; and supplying a developing solution to the developing solution supply portion simultaneously with the supply of the sample solution or prior to the supply of the sample solution. In the method, the flow of a sample solution in an undesired direction is a flow of the supplied sample solution in the direction toward the developing solution supply portion, and the flow of the supplied sample solution in the direction toward the developing solution supply portion is prevented by development of the supplied developing solution from upstream to downstream in the development member.

Still further, the method for preventing an increase in a background according to the present invention is a method for preventing an increase in a background in analysis using a sample analysis tool. The sample analysis tool includes=a development member including a developing solution supply portion, a sample supply portion, and a detection portion provided in this order from upstream to downstream along a flow of a developing solution. The method includes the steps of: supplying a sample solution containing a sample to the sample supply portion; and supplying a developing solution to the developing solution supply portion simultaneously with the supply of the sample solution or prior to the supply of the sample solution. In the method, by development of the supplied developing solution from upstream to downstream in the development member in the presence of a labeled substance that specifically binds to an analyte, detection of a label in any portion other than the detection portion caused by an upstream movement of the supplied sample solution is prevented.

Effects of the Invention

According to the present invention, it is possible to prevent the increase in a background in a simple manner without cost.

MODE FOR CARRYING OUT THE INVENTION

Figure 6D:
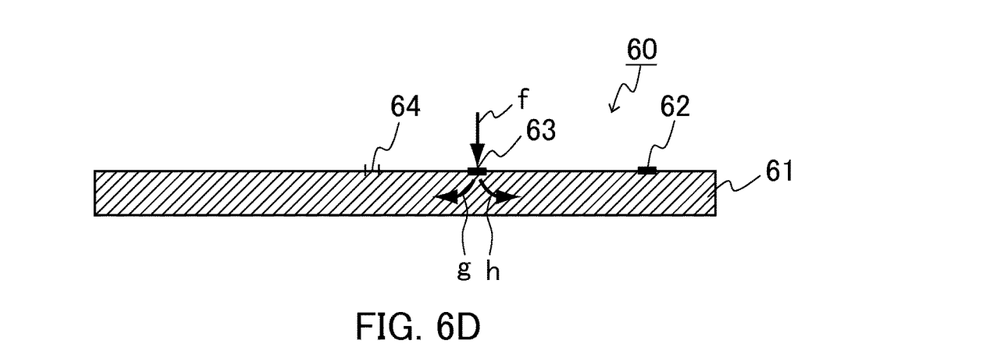
FIG. 6D is a sectional view for illustrating a conventional enzyme immunoassay method.

In order to achieve the above object, the inventors of the present invention conducted a series of studies. As a result, the inventors of the present invention clarified the cause of the increase in a background in a conventional immunoassay method, which is one example of an analysis method in which specifically binding substances are used. Specifically, in the conventional immunoassay method, a sample solution is supplied before supplying a developing solution. The move of the sample solution in the conventional immunoassay method will be described with reference to the sectional view of FIG. 6D. In FIG. 6D, the same components and portions as those in FIGS. 6A to 6C are given the same reference numerals. As shown in FIG. 6D, when the sample solution is supplied (the arrow f), the sample solution not only flows in the direction toward the detection portion 64 (the arrow g) but also flows in the direction toward the developing solution supply portion 62 (the arrow h) by the capillary action of the development member 61. Owing to this flow of the supplied sample solution in the direction toward the developing solution supply portion (a flow of a sample solution in an undesired direction, hereinafter, such flow simply is referred to as a "back-flow"), the antibody of the labeled antibody reacts with the antigen in the sample solution. Thus, the color development, light emission, or the like is caused in a portion other than the detection portion 64, resulting in an increase in a background. The increase in a background caused by this back-flow of the sample solution occurs generally in any analysis method in which specifically binding substances are used. Based on this finding, the inventors of the present invention conducted further studies. As a result, they found out that, by supplying the developing solution simultaneously with the supply of the sample solution or prior to the supply of the sample solution, it is possible to prevent the sample solution from flowing in the direction toward the developing solution supply portion, thereby achieving the present invention. According to the present invention, it is not necessary to increase the size of the development member or to provide a sample solution holding member, so that the increase in a background can be prevented in a simple manner without cost. Moreover, according to the present invention, even when the amount of a sample solution is increased, it is possible to prevent the increase in a background, so that, for example, the analysis accuracy can be further improved.

Each of the specifically binding substances may be selected as appropriate depending on the analyte, for example. It may be a substance derived from a living organism or a substance produced (synthesized) artificially.

Examples of the specifically binding substance include antibodies, antigens, and probes.

The sample analysis tool used in the analysis method, the method for preventing a back-flow of a sample solution, and the method for preventing an increase in a background according to the present invention may be configured so that, for example, the sample analysis tool includes a plurality of the sample supply portions and a plurality of the detection portions, and the plurality of the sample supply portions and the plurality of the detection portions are provided for one developing solution supply portion.

The analysis method, the method for preventing a back-flow of a sample solution, and the method for preventing an increase in a background according to the present invention may be configured so that, for example, the sample analysis tool further includes a case including a developing solution supply port and a sample supply port, and the development member is disposed in the case.

The analysis method, the method for preventing a back-flow of a sample solution, and the method for preventing an increase in a background according to the present invention may be configured so that, for example: the sample analysis tool further includes a first developing solution receiving pad disposed to be in contact with an upstream side of the development member. In the sample analysis tool, by supplying the developing solution to the first developing solution receiving pad, the developing solution develops to the development member.

The analysis method, the method for preventing a back-flow of a sample solution, and the method for preventing an increase in a background according to the present invention may be configured so that, for example, the sample analysis tool further includes a second developing solution receiving pad disposed to be in contact with a downstream side of the development member with respect to the detection portion.

The analysis method, the method for preventing a back-flow of a sample solution, and the method for preventing an increase in a background according to the present invention may be configured so that, for example, the immobilized substance that specifically binds to the analyte and the labeled substance that specifically binds to the analyte each are an antigen or an antibody.

The method for preventing a back-flow of a sample solution according to the present invention may be configured so that, for example: the sample analysis tool further includes a detection portion provided in a downstream side with respect to the sample supply portion along the flow of the developing solution; a substance that specifically binds to an analyte in the sample is immobilized in the detection portion; the supplied sample solution is introduced to the detection portion by development of the supplied developing solution in the development member in the presence of a labeled substance that specifically binds to the analyte; a complex containing the immobilized substance that specifically binds to the analyte, the analyte, and the labeled substance is formed in the detection portion, and the analyte is analyzed by detecting a label in the complex.

The method for preventing an increase in a background according to the present invention may be configured so that, for example: the method further includes the step of analyzing the analyte by detecting a label in a complex. In the method, a substance that specifically binds to the analyte in the sample is immobilized in the detection portion; the supplied sample solution is introduced to the detection portion by development of the supplied developing solution in the development member in the presence of the labeled substance that specifically binds to the analyte; and the complex containing the immobilized substance that specifically binds to the analyte, the analyte, and the labeled substance is formed in the detection portion.

Next, the analysis method, the sample analysis tool, the method for preventing a back-flow of a sample solution, and the method for preventing an increase in a background according to the present invention will be described in detail with reference to, as an illustrative example, an immunoassay method, which is one technique for conducting analysis using specifically binding substances. It is to be noted, however, the present invention is not limited only to the immunoassay method to be described below. In FIGS. 1 to 6 to be described below, common components and portions are given the same reference numerals. In the drawings, for the sake of simplicity in illustration, the structure of each component and portion may be simplified as appropriate, and the size or the like of each component and portion may be different from the actual size or the like.

(First Embodiment)

An analysis method according to the present embodiment is an immunoassay method (enzyme immunoassay method) in which an immobilized antibody is used as the "immobilized specifically binding substance" and a labeled antibody labeled with an enzyme (an enzyme-labeled antibody) is used as the "labeled specifically binding substance". The same applied to the second and third embodiments to be described below. Furthermore, a sample analysis tool used in the immunoassay method of the present embodiment is an example of the sample analysis tool of the present invention. It is to be noted, however, the sample analysis tool of the present invention is not limited to this illustrative example.

Figure 1A:
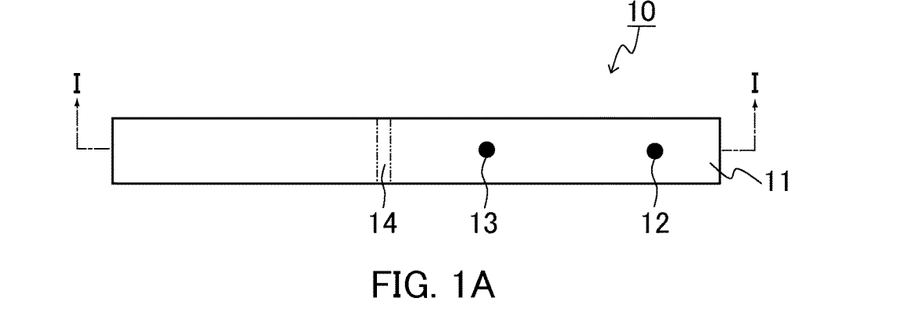
FIG. 1A is a plan view showing an example of the configuration of a sample analysis tool used in one embodiment of the present invention.
Figure 1B:
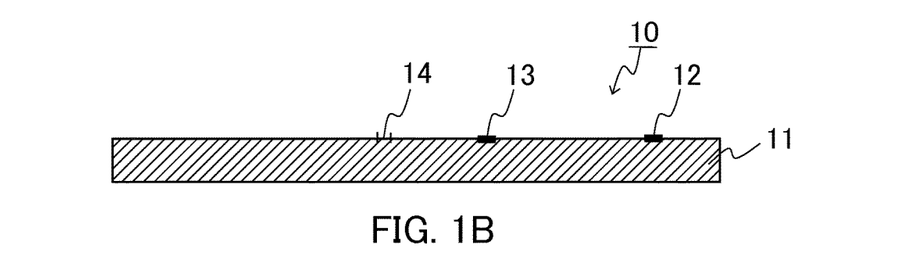
FIG. 1B is a sectional view of the sample analysis tool, viewed along arrows I-I in FIG. 1A.

FIGS. 1A and 1B show an example of the configuration of the sample analysis tool used in the immunoassay method of the present embodiment. FIG. 1A is a plan view showing the sample analysis tool used in the present embodiment. FIG. 1B is a sectional view of the sample analysis tool, viewed along arrows I-I in FIG. 1A. As shown in FIGS. 1A and 1B, this sample analysis tool 10 includes a development member 11. In the development member 11, a developing solution supply portion 12, a sample supply portion 13, and a detection portion 14 are provided in this order from upstream to downstream along the flow of a developing solution (from the right to the left in FIGS. 1A and 1B). In this sample analysis tool 10, the developing solution supply portion 12, the sample supply portion 13, and the detection portion 14 are predetermined regions in the development member 11. An antibody is immobilized in the detection portion 14 (immobilized antibody). Although this sample analysis tool 10 has a single detection portion 14, the configuration of the sample analysis tool 10 is not limited thereto. The sample analysis tool 10 may have a plurality of detection portions depending on the number of items (antigens) to be analyzed and the like, for example.

The development member is not particularly limited as long as it has a porous structure exhibiting a capillary action. The material forming the development member may be a porous membrane, a granular substance, particulate powder, or the like, for example. Examples of the porous membrane include: cellulose membranes; membranes formed of cellulose derivatives such as cellulose acetate and nitrocellulose; glass filters; and filter papers. Examples of the granular substance or the particulate powder include polymer beads, glass beads, titanium dioxide, cellulose, salts, and hydrophobized polysaccharides. The size of the development member is not particularly limited, and can be set as appropriate depending on the specification and the like of an analyzer, for example.

The immobilized antibody is not particularly limited as long as it is an antibody that binds to an antigen as an analyte in a sample. The antibody can be set as appropriate depending on an antigen and the like to be described below. The antibody may be derived from a living organism or synthesized artificially, for example. Examples of the antibody derived from a living organism include immunogloblins (Ig), antibody fragments, and chimeric antibodies. Examples of the immunogloblins include IgG, IgA, IgM, IgE, and IgD. Examples of the antibody fragments include Fab, Fab', and F(ab')2. Examples of the chimeric antibodies include humanized antibodies. The antibody may be derived from animal species such as mammals like mice, rabbits, cows, pigs, horses, sheep, and goats; birds such as chickens; and humans, for example, and are not particularly limited. The antibody may be produced from serum derived from any of the above-described animal species by a conventionally known method, or any of various kinds of commercially available antibodies may be used as the antibody, and they are not particularly limited. As the antibody, either of a polyclonal antibody and a monoclonal antibody may be used, for example. Examples of the artificially-synthesized antibodies include affibodies. A method for immobilizing the antibody on the detection portion may be such that, for example, applying an antibody solution containing the antibody to the development member such as a porous membrane using an applicator, and then air drying the solution using a dryer or the like.

In the present invention, the sample analysis tool may be a commercially available product or may be self-produced, for example.

In the present invention, the sample solution is not particularly limited as long as it contains a sample. The sample is not particularly limited, and examples thereof include biological samples and food. The sample may be in the form of liquid, or the sample in the form of solid may be, for example, dissolved, suspend, or dispersed in a buffer or the like. Examples of the liquid biological sample include nasal aspirate, nasal lavage fluid, nasal swab, nasal secretion, throat swab, oral rinse, saliva, whole blood, serum, plasma, sweat, and urine. Examples of the solid biological sample include cells and feces. Examples of the food include: food substances such as animals and plants; and processed food. The buffer is not particularly limited, and examples thereof include a Tris buffer, a phosphate buffer, an acetic acid buffer, and a boric acid buffer. The pH of the buffer is not particularly limited, and is in the range from 4 to 10, preferably from 6 to 9, for example.

In the immunoassay method of the present embodiment, an analyte in the sample is an antigen that binds to the above-described immobilized antibody and labeled antibody. Examples of the antigen include, but not particularly limited to: biogenic substances including pathogen antigens, antibodies, cancer markers, and hormones, such as influenza A viruses, influenza B viruses, influenza C viruses, adenoviruses, RS viruses, coronaviruses, astroviruses, noroviruses, measles viruses, rotaviruses, human immunodeficiency viruses (HIV), human T-cell leukemia viruses (HTLV-1), hepatitis B viruses (HBV), hepatitis C viruses (HCV), herpesviruses, *Mycoplasma, Treponema pallidum, Chlamydia trachomatis*, tubercle bacilli, coliform bacteria, group A streptococci, group B streptococci, *Streptococcus pneumoniae*, staphylococci, MRSA, *Legionella*, enterohemorrhagic *Escherichia coli* O157, verotoxin, *Salmonella, Clostridium difficile, Helicobacter pylori*, CRP, HBs antigens, HBs antibodies, HBc antigens, HBc antibodies, HBe antigens, HBe antibodies, prostate-specific antigens (PSA), human chorionic gonadotrophin (hCG), luteinizing hormone (LH), troponin T, troponin I, myoglobin, D-dimer, fecal hemoglobin, hemoglobin A1c, and IgE antibodies; residual agricultural chemicals; environment hormones; and allergic substances in food.

The sample solution may contain a buffer, a surfactant, an antibacterial agent, and the like, for example. The buffer is not particularly limited, and examples thereof include the above-described buffers. The surfactant is not particularly limited, and examples thereof include anionic surfactants, nonionic surfactants, and amphoteric surfactants. The antibacterial agent is not particularly limited, and examples thereof include sodium azide, 5-chloro-2-methyl-4-isothiazoline-3-one, and 2-methyl-4-isothiazoline-3-one.

The enzyme-labeled antibody is not particularly limited as long as it is an enzyme-labeled antibody that binds to an antigen as an analyte in the sample. Examples of the antibody of the enzyme-labeled antibody include those described above as examples of the antibody of the immobilized antibody.

The enzyme of the enzyme-labeled antibody is not particularly limited, and examples thereof include peroxidase, alkaline phosphatase, and β-D-galactosidase. The method for preparing the enzyme-labeled antibody is not particularly limited, and a conventionally known method may be used, for example.

The enzyme-labeled antibody may be contained in the sample solution, or the development member, a pad provided additionally, or the like may be impregnated with the enzyme-labeled antibody, for example. However, for example, since it is possible to perform analysis with higher sensitivity without providing the pad or the like additionally, it is preferable that the enzyme-labeled antibody is contained in the sample solution.

As the developing solution, a buffer such as a Tris buffer, a phosphate buffer, an acetic acid buffer, a boric acid buffer, or the like may be used, for example. To the developing solution, a stabilizer, an antibacterial agent, and the like may be added as appropriate, for example. Furthermore, the amount of the developing solution to be supplied can be set as appropriate depending on the amount of the sample solution to be supplied and the like, for example.

In the immunoassay method of the present embodiment, by the development of the developing solution, the substrate can be introduced to the detection portion from the developing solution supply portion via the sample supply portion. The substrate is not particularly limited as long as it, for example, develops color or emits light when reacting with the enzyme, for example. The kind of the substrate is not particularly limited, and can be selected depending on the kind of the enzyme used in the enzyme-labeled antibody, for example. Specific examples of the substrate include 2,2'-azino-bis(3-ethylbenzothiazoline-6-sulfonic acid) (ABTS), 3,3',5,5'-tetramethylbenzidine (TMB), diaminobenzidine (DAB), 5-bromo-4-chloro-3-indolylphosphate (BCIP), 4-methylumbelliferyl-β-D-galactoside (4MUG), and 3-(2'-spiroadamantane)-4-methoxy-4-(3"-β-D-galactopyranosyl) phenyl-1,2-dioxetane (AMGPD).

The substrate may be contained in at least one of the developing solution and the sample solution, or the development member or the like may be impregnated with the substrate, for example. When impregnating the development member or the like with the substrate, a portion between the sample supply portion and the detection portion or a portion between the developing solution supply portion and the sample supply portion on the development member may be impregnated with the substrate, for example.

Figure 3A:
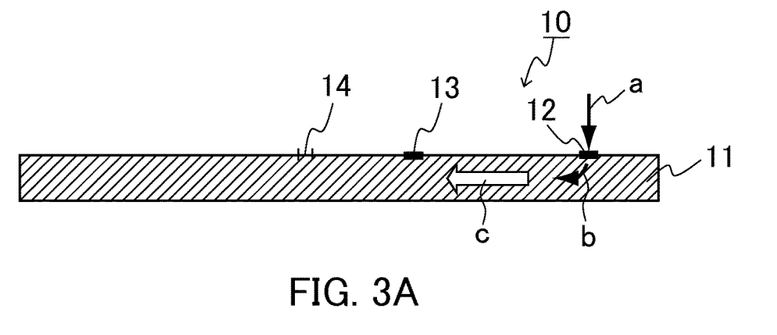
FIGS. 3A to 3C are sectional views for illustrating an immunoassay method in the embodiment of the present invention.
Figure 3B:
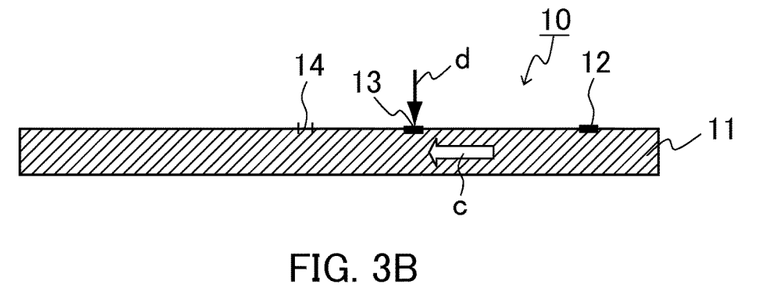
Figure 3C:
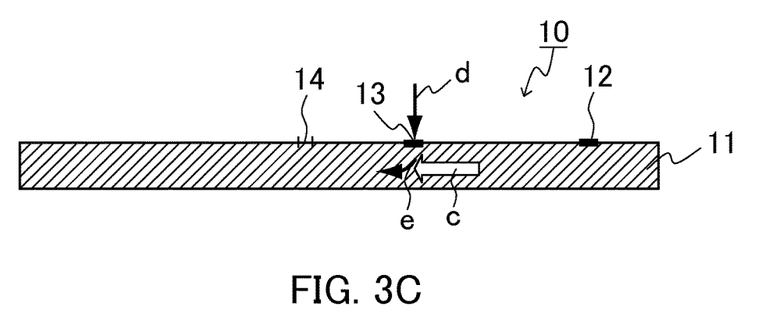
Figure 3D:
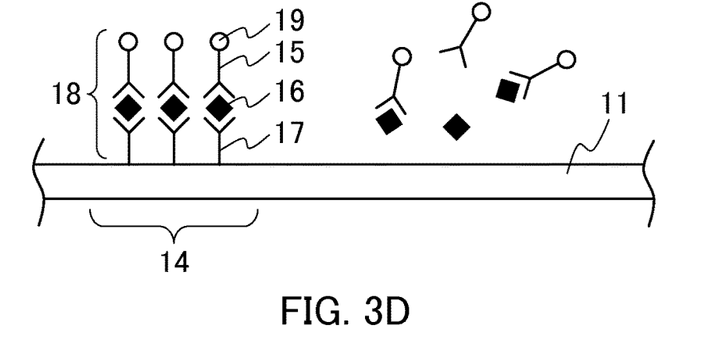
FIG. 3D is a schematic view for illustrating the detection of an antigen in a detection portion.

Next, the immunoassay method of the present embodiment will be described with reference to FIG. 3. FIGS. 3A to 3C are sectional views showing the sample analysis tool. FIG. 3D is a schematic view for illustrating the detection of the antigen in the detection portion.

As shown in FIG. 3A, first, the developing solution is supplied to the developing solution supply portion 12 (the arrow a). The supplied developing solution permeates the development member 11, as indicated with the arrow b. The developing solution having permeated the development member 11 develops from upstream to downstream in the development member 11 toward the detection portion 14 (to the left in FIG. 3A) in the development member 11, as indicated with the arrow c. At this time, in the case where a portion in the vicinity of the developing solution supply portion in the development member is impregnated with the above-described substrate, the substrate moves toward the detection portion by the development of the developing solution. The substrate may be mixed in the developing solution before being supplied.

Next, as shown in FIG. 3B, the sample solution is supplied to the sample supply portion 13 (the arrow d). At this time, the supplied sample solution spontaneously develops in all the directions in the development member. However, as shown in FIG. 3C, by the development of the developing solution supplied prior to the supply of the sample solution (the arrow c), the sample solution is caused to develop in the direction toward the detection portion 14, as indicated with the arrow e. Thus, it is possible to prevent the back-flow toward the developing solution supply portion 12 provided in the upstream side of the development member 11 (to the right in FIG. 3C). Note here that the expression "prevent the back-flow" not only means that the back-flow of the sample solution is prevented completely, but also encompasses that, for example, the back-flow of the sample solution is prevented to the extent that the increase in a background is prevented as compared with the case where the sample solution is supplied to the sample supply portion prior to the supply of the developing solution. The enzyme-labeled antibody may be mixed in the sample solution before being supplied, or a portion in the vicinity of the sample supply portion in the development member may be impregnated with the enzyme-labeled antibody. In the above-described manner, in the development member 11, the developing solution develops (the arrow c) in the presence of the enzyme-labeled antibody, whereby the substrate and the sample solution are introduced to the detection portion 14.

Thus, as shown in FIG. 3D, a complex 18 of the immobilized antibody 17, the antigen 16 as the analyte in the sample, and the enzyme-labeled antibody 15 is formed in the detection portion 14. In the detection portion 14, color development, light emission, or the like caused by the reaction between an enzyme 19 of the complex 18 (the enzyme-labeled antibody 15) and the substrate is detected. This allows the antigen 16 to be detected indirectly. The detection may be performed by determination through visual observation or may be performed with the use of a colorimeter, a fluorometer, a photon counter, a photosensitive film, or the like, for example. In the above described manner, the occurrence of color development, light emission, or the like in any portion other than the detection portion 14 due to the movement of the supplied sample solution toward the upstream side of the development member is prevented. As a result, the increase in a background is prevented, whereby a highly-sensitive immunoassay (quantitative analysis, semi-quantitative analysis, qualitative analysis, or the like) becomes possible. Note here that the expression "an increase in a background is prevented" not only means that the increase in a background is prevented completely, but also encompasses that, for example, the increase in a background is prevented as compared with the case where the sample solution is supplied to the sample supply portion prior to the supply of the developing solution.

Although the developing solution is supplied prior to the supply of the sample solution in the immunoassay method of the present embodiment, the immunoassay method is not limited thereto. The same effect can be obtained when the developing solution is supplied simultaneously with the supply of the sample solution. Furthermore, when the developing solution is supplied prior to the supply of the sample solution, for example, it is possible to further improve the above-described effect by considering the timing of supplying the sample solution (e.g., supplying the sample solution immediately before the developing solution reaches the sample supply portion) or the like. The timing can be set as appropriate depending on, for example, the distance between the developing solution supply portion and the sample supply portion, the kind of the developing solution, or the kind, size and the like of the development member. When the distance between the developing solution supply portion and the sample supply portion is in the range from 1 to 100 mm, the sample solution is supplied to the sample supply portion after a lapse of 0 to 400 seconds from the supply of the developing solution to the developing solution supply portion, for example. When the distance is in the range from 10 to 80 mm, it is preferable that the sample solution is supplied to the sample supply portion after a lapse of 0 to 360 seconds from the supply of the developing solution to the developing solution supply portion. When the distance is in the range from 20 to 40 mm, it is more preferable that the sample solution is supplied to the sample supply portion after a lapse of 0 to 180 seconds from the supply of the developing solution to the developing solution supply portion. When the distance is 30 mm, it is particularly preferable that the sample solution is supplied to the sample supply portion after a lapse of 30 seconds from the supply of the developing solution to the developing solution supply portion.

Furthermore, in the immunoassay method of the present embodiment, since the back-flow of the sample solution toward the developing solution supply portion can be prevented as described above, it is possible to increase the amount of the sample solution, for example. This allows the analysis accuracy to be further improved, for example.

In the present embodiment, in the case where the analyte in the sample is an antibody, the sample analysis tool may be configured so that, for example, the detection portion includes an immobilized antigen instead of the immobilized antibody. With this configuration, a complex of the enzyme-labeled antibody or enzyme labeled antigen, the antibody as the analyte in the sample, and the immobilized antigen is formed, and the enzyme contained in the complex reacts with the substrate, whereby color is developed or light is emitted, for example. By detecting this color development, light emission, or the like, it is possible to detect the antibody indirectly. The antibody as the analyte in the sample is not particularly limited, and examples thereof include various kinds of antibodies. An antigen of the immobilized antigen is not particularly limited as long as it can bind to the antibody as the analyte in the sample. An antibody of the enzyme-labeled antibody is not particularly limited as long as it can bind to the antibody as the analyte in the sample. Also, an antigen of the enzyme labeled antigen is not particularly limited as long as it binds to the antibody as the analyte in the sample. As a method for preparing the antibody of the enzyme-labeled antibody and a method for labeling the antibody, conventionally known methods can be used, and examples of the enzyme to be used are the same as those described above. Also, as a method for preparing the antigen of the enzyme-labeled antigen and a method for labeling the antigen, conventionally known methods can be used, and examples of the enzyme to be used are the same as those described above. A method for producing the immobilized antigen may be, for example, a conventionally known method or the like, and is not particularly limited. Also, a method for immobilizing the immobilized antigen to the detection portion may be, for example, a conventionally known method or the like, and is not particularly limited.

The sample analysis tool used in the immunoassay method of the present embodiment may further includes, for example, a developing solution receiving pad and a waste liquid absorbing pad, in order to accelerate the development of the developing solution. Also, the sample analysis tool used in the immunoassay method of the present embodiment may further include a support in order to maintain the shape of the sample analysis tool stably, for example.

Figure 2A:
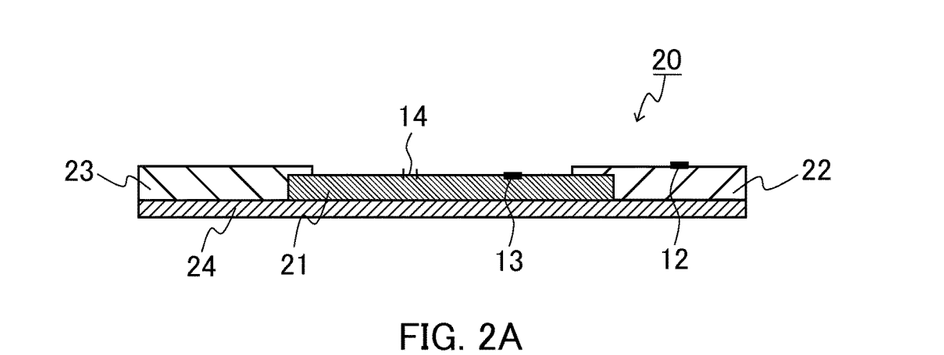
FIG. 2A is a sectional view showing another example of the configuration of the sample analysis tool used in the embodiment of the present invention.

FIG. 2A is a sectional view showing an example of the configuration of the sample analysis tool including the developing solution receiving pad, the waste liquid absorbing pad, and the support. As shown in FIG. 2A, this sample analysis tool 20 includes, as main components, a development member 21, a developing solution receiving pad 22, a waste liquid absorbing pad 23, and a support 24. The developing solution receiving pad 22 is disposed so as to be in contact with the upstream side of the development member 21 (the right side in FIG. 2A). The waste liquid absorbing pad 23 is disposed so as to be in contact with the downstream side of the development member 21 (the left side in FIG. 2A) with respect to the detection portion 14. The development member 21, the developing solution receiving pad 22, and the waste liquid absorbing pad 23 are disposed on the support 24. Except for the above, this sample analysis tool has the same configuration as the above-described sample analysis tool 10. The "developing solution receiving pad" corresponds to the "first developing solution receiving pad" of the present invention. The "waste liquid receiving pad" corresponds to the "second developing solution receiving pad" of the present invention.

The materials of the developing solution receiving pad and the waste liquid absorbing pad are not particularly limited, and examples thereof include polyethylene, glass fiber, rayon, nylon, paper, and cellulose. The shape and the size of the developing solution receiving pad are not particularly limited, and can be set as appropriate depending on the shape and the like of the development member, for example.

The material of the support is not particularly limited, and examples thereof include polyethylene terephthalate, polyethylene, polystyrene, polyester, and cellulose acetate. The shape of the support is not particularly limited, and examples thereof include a film-like shape, a sheet-like shape, and a plate-like shape. The shape and the size of the support are not particularly limited, and can be set as appropriate depending on the development member and the like.

The development member, the developing solution receiving pad, and the waste liquid absorbing pad can be disposed on the support by an ordinary method, for example. Specifically, they may be fixed on the support using a two-sided tape, an adhesive, or the like, for example.

In an immunoassay method using this sample analysis tool 20, the developing solution may be supplied to the developing solution receiving pad 22 disposed so as to be in contact with the upstream side of the development member 21 (the developing solution receiving pad 22 is integrated with the development member 21), for example. In this case, part of the developing solution receiving pad 22 serves as the developing solution supply portion 12. The developing solution supply portion 12 is a predetermined region in the developing solution receiving pad 22. With this configuration, the developing solution develops to the development member 21 via the developing solution receiving pad 22. Except for the above, the immunoassay method can be carried out in the same manner as the above-described immunoassay method. Furthermore, the developing solution receiving pad 22 may be impregnated with the substrate, for example.

(Second Embodiment)

Figure 2B:
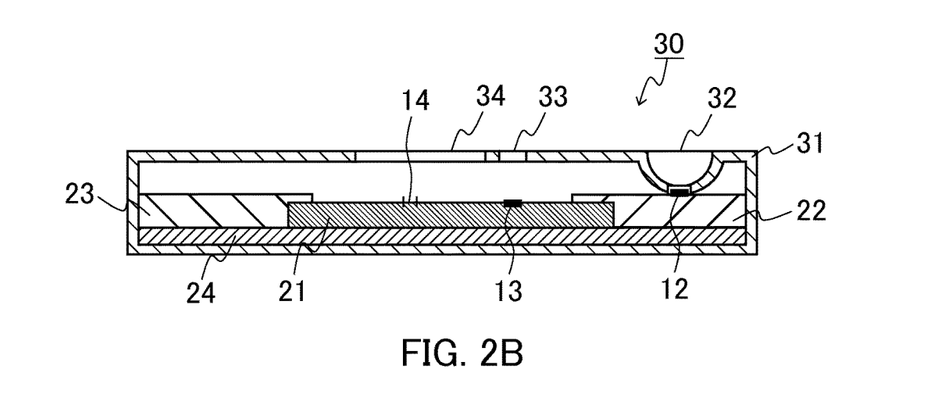
FIG. 2B is a sectional view showing still another example of the configuration of the sample analysis tool used in the embodiment of the present invention.

FIG. 2B is a sectional view showing an example of the configuration of a sample analysis tool used in an immunoassay method according to the present embodiment. As shown in FIG. 2B, this sample analysis tool 30 corresponds to the sample analysis tool shown in FIG. 2A, further including a case 31. The development member 21, the developing solution receiving pad 22, the waste liquid absorbing pad 23, and the support 24 are disposed in the case 31. The case 31 includes a developing solution supply port 32, a sample supply port 33, and a window 34. The developing solution supply port 32 is provided so that the lower end thereof is in contact with the developing solution supply portion 12. The sample supply port 33 is provided above the sample supply portion 13. The window 34 is provided above the detection portion 14. With such a configuration, for example, the sample analysis tool can be handled more easily, so that the operability of the sample analysis tool is improved. Although this sample analysis tool 30 is configured so that the developing solution supply portion 12 (the developing solution receiving pad 22) is in contact with the lower end of the developing solution supply port 32, the configuration of the sample analysis tool 30 is not limited thereto.

The material of the case is not particularly limited, and examples thereof include polyethylene, polystyrene, polypropylene, and synthetic resins obtained by copolymerization of acrylonitrile, butadiene, and styrene. The shape and the size of the case are not particularly limited, and can be set as appropriate depending on the shape and the size of the development member and the like, for example.

Next, the immunoassay method of the present embodiment will be described.

In the immunoassay method of the present embodiment, first, the developing solution is supplied to the developing solution supply port 32, whereby the developing solution is supplied to the developing solution supply portion 12. Next, the sample solution is supplied to the sample supply port 33, whereby the sample solution is supplied to the sample supply portion 13. The result of the detection in the detection portion 14 is observed through the window 34. Except for the above, the immunoassay method can be carried out in the same manner as the immunoassay method using the sample analysis tool shown in FIG. 2A.

(Third Embodiment)

An immunoassay method of the present embodiment is an example of an immunoassay method carried out using a sample analysis tool capable of analyzing a plurality of items.

Figure 4A:
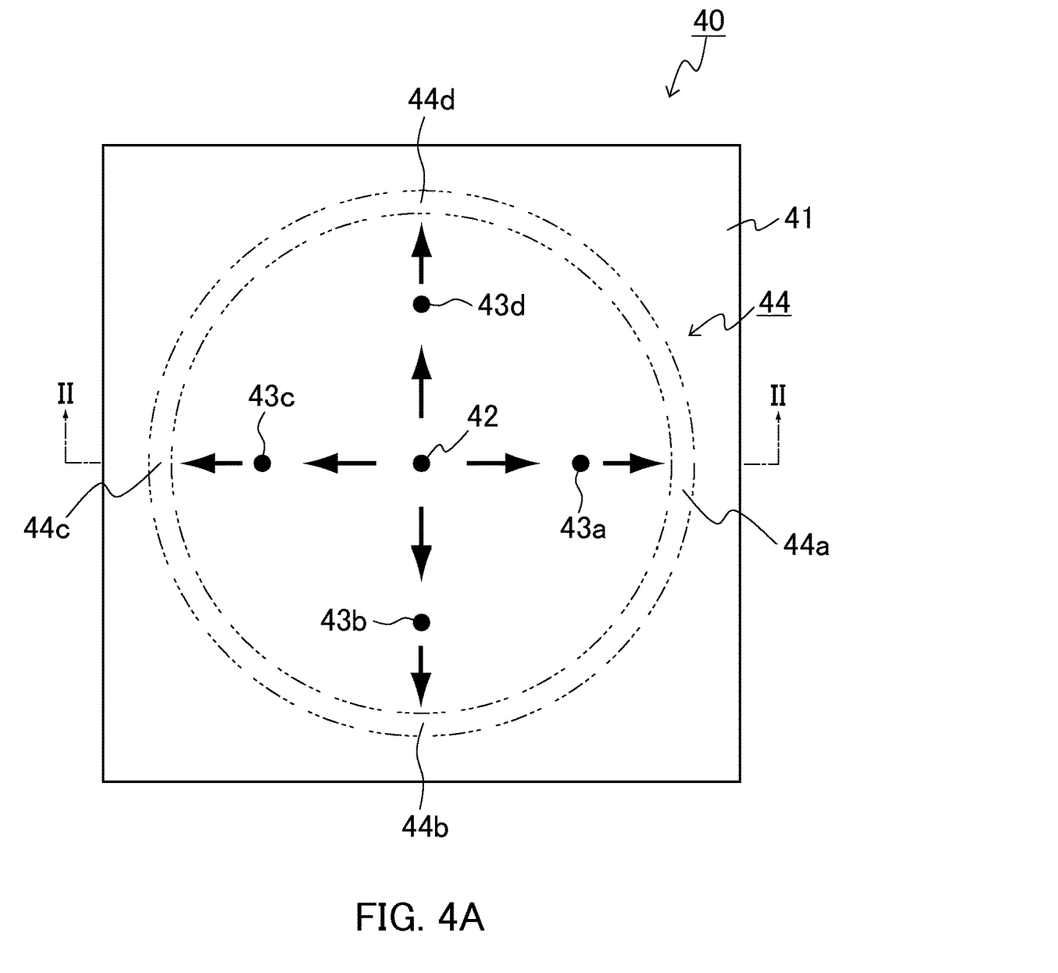
FIG. 4A is a plan view showing still another example of the configuration of the sample analysis tool used in the embodiment of the present invention.
Figure 4B:
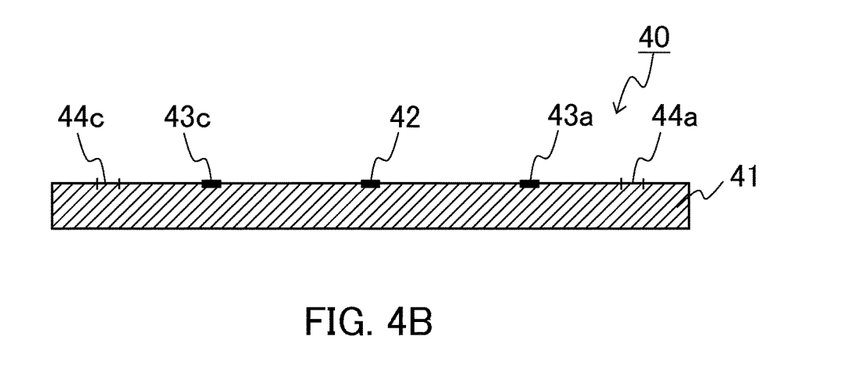
FIG. 4B is a sectional view showing the sample analysis tool, viewed along arrows II-II in FIG. 4A.

FIG. 4 shows an example of the configuration of a sample analysis tool used in the immunoassay method of the present embodiment. FIG. 4A is a plan view showing the sample analysis tool used in the present embodiment. FIG. 4B is a sectional view showing the sample analysis tool, viewed along arrows II-II in FIG. 4A. As shown in FIGS. 4A and 4B, this sample analysis tool 40 has a development member 41 in a square shape. In a central portion of the development member 41, one developing solution supply portion 42 is provided. With respect to the developing solution supply portion 42, four sample supply portions 43a, 43b, 43c, and 43d are provided around the developing solution supply portion 42 as their center so as to be closer to four end faces (shown on the top, bottom, right, and left in FIG. 4A) of the development member 41. On the outside of the sample supply portions 43a, 43b, 43c, and 43d, a ring-shaped detection portion 44 is provided. In this sample analysis tool 40, in a portion of the detection portion 44 located on an extended line extending outwardly from the straight line connecting the developing solution supply portion 42 and the sample supply portion 43a, a detection portion 44a is provided in relation to the sample supply portion 43a. In a portion of the detection portion 44 located on an extended line extending outwardly from the straight line connecting the developing solution supply portion 42 and the sample supply portion 43b, a detection portion 44b is provided in relation to the sample supply portion 43b. In a portion of the detection portion 44 located on an extended line extending outwardly from the straight line connecting the developing solution supply portion 42 and the sample supply portion 43c, a detection portion 44c is provided in relation to the sample supply portion 43c. In a portion of the detection portion 44 located on an extended line extending outwardly from the straight line connecting the developing solution supply portion 42 and the sample supply portion 43d, a detection portion 44d is provided in relation to the sample supply portion 43d. Antibodies are immobilized in the respective detection portions 44a, 44b, 44c, and 44d (immobilized antibodies). Except for the above, this sample analysis tool has the same configuration as the sample analysis tool shown in FIGS. 1 and 2. With this configuration, it becomes possible to detect a plurality of items in a single analysis, for example. There may be two or more developing solution supply portions. In this case, with respect to one of the developing solution supply portions, a plurality of sample supply portions and a plurality of detection portions may be provided.

Next, the immunoassay method of the present embodiment will be described with reference to FIG. 4A.

As shown in FIG. 4A, when the developing solution is supplied to the developing solution supply portion 42, the developing solution develops in the development member 41 radially toward the respective detection portions 44a, 44b, 44c, and 44d via the respective sample supply portions 43a, 43b, 43c, and 43d, as indicated with arrows, accompanied with the sample and the like. Except for the above, the immunoassay method can be carried out in the same manner as the immunoassay method of the first or second embodiment.

Figure 5:
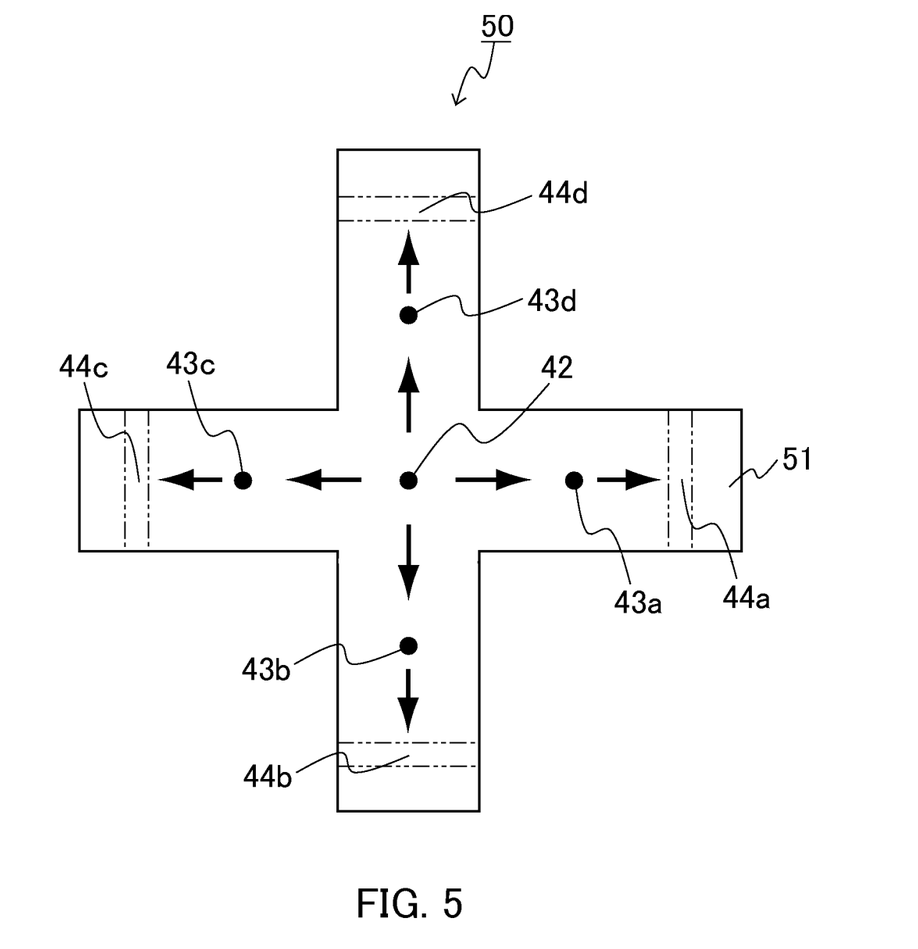
FIG. 5 is a plan view showing still another example of the configuration of the sample analysis tool used in the embodiment of the present invention.

Although the ring-shaped detection portion 44 is provided in the square development member 41 in the sample analysis tool 40, the configuration of the sample analysis tool is not limited to thereto. For example, the sample analysis tool may be configured so as to include a cross-shaped development member as shown in FIG. 5. This sample analysis tool 50 has a cross-shaped development member 51. In the central portion of the cross-shaped development member 51, one developing solution supply portion 42 is provided. Four sample supply portions 43a, 43b, 43c, and 43d are provided around the developing solution supply portion 42 as their center so as to be closer to four end faces (shown on the top, bottom, right, and left in FIG. 5) of the development member 51. On an extended line extending outwardly from the straight line connecting the developing solution supply portion 42 and the sample supply portion 43a, a detection portion 44a is provided in relation to the sample supply portion 43a. On an extended line extending outwardly from the straight line connecting the developing solution supply portion 42 and the sample supply portion 43b, a detection portion 44b is provided in relation to the sample supply portion 43b. On an extended line extending outwardly from the straight line connecting the developing solution supply portion 42 and the sample supply portion 43c, a detection portion 44c is provided in relation to the sample supply portion 43c. On an extended line extending outwardly from the straight line connecting the developing solution supply portion 42 and the sample supply portion 43d, a detection portion 44d is provided in relation to the sample supply portion 43d. Except for the above, the sample analysis tool 50 has the same configuration as the above-described sample analysis tool 40. The development of the developing solution in an immunoassay method using this sample analysis tool 50 is the same as that in the immunoassay method using the sample analysis tool 40.

(Fourth Embodiment)

An analysis method according to the present embodiment is an immunoassay method in which colored insoluble carrier particles are used as a label of a labeled antibody.

The colored insoluble carrier particles are not particularly limited, and examples thereof include colored latex particles, metal colloid particles, colored polymethyl methacrylate particles, colored polylactic acid particles, colored porous glass particles, colored silica particles, colored agarose particles, and colored dextran particles. The colored latex particles are not particularly limited, and examples thereof include blue latex particles and red latex particles. The metal colloid particles are not particularly limited, and examples thereof include gold colloid particles and platinum colloid particles.

The labeled antibody having the colored insoluble carrier particles bound thereto is not particularly limited. For example, the labeled antibody can be prepared by suspending the colored insoluble carrier particles in a buffer or the like, and adding the antibody to this suspension so as to cause a reaction between them. The buffer is not particularly limited, and examples thereof include the above-described buffers.

In the immunoassay method of the present embodiment, for example, the labeled antibody having the colored insoluble carrier particles bound thereto may be contained in the sample solution, or the development member, a pad provided additionally, or the like may be impregnated with the labeled antibody having the colored insoluble carrier particles bound thereto, for example. However, for example, since it is possible to perform analysis with higher sensitivity without providing the pad or the like additionally, it is preferable that the labeled antibody having the colored insoluble carrier particles bound thereto is contained in the sample solution.

In the immunoassay method of the present embodiment, by detecting coloring caused by the agglutination of the colored insoluble carrier particles in the detection portion, the antigen as the analyte is detected. Except for the above, the immunoassay method can be carried out in the same manner as the immunoassay methods described in the first to third embodiments. In the present embodiment, no substrate is used. The detection may be performed by determination through visual observation or may be performed with the use of colorimeter or the like, for example.

(Fifth Embodiment)

An analysis method according to the present embodiment is an immunoassay method in which a fluorescent dye is used as a label of a labeled antibody The fluorescent dye is not particularly limited, and examples thereof include FITC. When an antibody or antigen labeled with a fluorescent dye is used, for example, a complex of the immobilized antibody, an antigen as the analyte, and the labeled antibody, or a complex of the immobilized antigen, an antibody as an analyte, and the labeled antibody or labeled antigen is formed, and light emitted by the fluorescent dye in the labeled antibody or labeled antigen can be detected by irradiating the complex with excitation light.

EXAMPLES

Next, examples of the present invention will be described together with comparative examples. It is to be noted, however, the present invention is by no means limited or restricted by the following examples and comparative examples.

Example 1

(Production of Sample Analysis Tool)

A sample analysis tool 20 having the configuration shown in FIG. 2A was produced in the following manner.

(1) Production of Development Member

A nitrocellulose membrane (Millipore Corporation, trade name "HA180") was cut into a piece having a length of 50 mm and a width of 4 mm. This piece was used as a development member 21. At a distance of 31 mm from one end of the development member 21 (the right end in FIG. 2A), an aqueous solution of a protein extracted from egg white allergen (the aqueous solution obtained by diluting the protein with a 1 mg/ml (5 mmol/l) boric acid buffer (pH 8.5) and then dialyzing it) was applied so as to form a line with a width of 1 mm. Thus, a detection portion 14 in which the antibody was immobilized was formed in a surface of the development member 21.

(2) Production of Developing Solution Receiving Pad

A cellulose pad (Millipore Corporation, trade name "AP25") was cut into a piece having a length of 20 mm and a width of 4 mm. This piece was used as a developing solution receiving pad 22. At a distance of 10 mm from one end of the developing solution receiving pad 22 (the right end in FIG. 2A), 5 μl of 5-bromo-4-chloro-3-indolyl phosphate (20 mg/ml, Boehringer Mannheim, trade name "BCIP") was applied as a substrate, which was allowed to stand at 37° C. for 1 hour so as to be dried.

(3) Production of Waste Liquid Absorbing Pad

A cellulose pad (Millipore Corporation, trade name "AP25") was cut into a piece having a length of 30 mm and a width of 4 mm. This piece was used as a waste liquid absorbing pad 23.

(4) Production of Support

A backing sheet (BioDot Inc., PET) was cut into a piece having a length of 80 mm and a width of 4 mm. This piece was used as a support 24.

(5) Production of Sample Analysis Tool

The development member 21 was attached to a portion at a distance of 10 mm from one end of the support 24 (the right end in FIG. 2A). Next, one end of the developing solution receiving pad 22 (the right end in FIG. 2A) was fixed to one end of the support 24, and a portion on the other end side of the developing solution receiving pad 22 (the left end portion in FIG. 2A) was laid over a portion on the upstream side of the development member 21. Then, one end of the waste liquid absorbing pad 23 (the left end in FIG. 2A) was fixed to the other end of the support 24 (the left end in FIG. 2A), and a portion on the other end side of the waste liquid absorbing pad 23 (the right end portion in FIG. 2A) was laid over the other end portion of the development member 21 (the left end portion in FIG. 2A, which is on the downstream side with respect to the detection portion 14). Thus, the sample analysis tool 20 according to the present example was produced. The developing solution supply portion 12 was provided at a distance of 5 mm from the above-mentioned one end of the developing solution receiving pad 22. The sample supply portion 13 was provided at a distance of 25 mm from the above-mentioned one end of the development member 21. The distance between the developing solution supply portion 12 and the sample supply portion 13 was set to 30 mm.

(Immunoassay Using Sample Analysis Tool)

(1) Preparation of Sample Solution

Three sample solutions (sample solutions 1 to 3) were prepared by adding 60 μl of alkaline phosphatase-labeled antibody (enzyme-labeled antibody, 10 μg, derived from a goat) to 10 μl of egg white-specific IgE positive serum.

(2) Preparation of Developing Solution 0.1 mol/l sodium carbonate/sodium hydrogencarbonate buffer (pH: 10.0) was prepared. This buffer was used as a developing solution.

(3) Carrying Out Analysis Method

First, 100 μl of the developing solution was supplied to the developing solution supply portion 12. Next, after a lapse of about 30 seconds from the supply of the developing solution, 15 μl of the sample solution was supplied to the sample supply portion 13. Thereafter, the reflectance in the detection portion was measured using an immunoassay device (ARKRAY, Inc., trade name "SPOTCHEM IL SL-4720"). The reflectances (%) obtained when using the three types of samples in the present example are shown in Table 1 below. The smaller the reflectance became, the more significantly the increase in a background was prevented.

Example 2

Sample analysis was carried out in the same manner as in Example 1, except that 30 μl of each of the sample solutions was supplied. The reflectances (%) obtained when using the three samples in the present example are shown in Table 1 below.

Comparative Example 1

First, 15 μl of each of the sample solutions was supplied to the sample supply portion 13. Then, sample analysis was carried out in the same manner as in Example 1, except that 100 μl of the developing solution was supplied to the developing solution supply portion 12 after a lapse of about 30 seconds from the supply of the sample solution. The reflectances (%) obtained when using the three samples in the present comparative example are shown in Table 1 below.

Comparative Example 2

First, 30 µl of each of the sample solutions was supplied to the sample supply portion 13. Next, sample analysis was carried out in the same manner as in Example 2, except that 100 µl of the developing solution was supplied to the developing solution supply portion 12 after a lapse of about 30 seconds from the supply of the sample solution. The reflectances (%) obtained when using the three samples in the present comparative example are shown in Table 1 below.

TABLE 1

|  | Ex. 1 | Ex. 2 | Comp. Ex. 1 | Comp. Ex. 2 |
|---|---|---|---|---|
| Sample solution 1 | 48.7 | 46.9 | 51.7 | 95.4 |
| Sample solution 2 | 58.0 | 57.3 | 59.5 | 99.1 |
| Sample solution 3 | 68.0 | 65.8 | 69.1 | 100 |

(Evaluation)

As can be seen from Table 1 above, in Example 1 in which 15 µl of the sample solutions were supplied after the supply of the developing solution, the reflectances were smaller than those in Comparative Example 1 in which the developing solution was supplied after the supply of the same amount of the sample solutions. This indicates that the increase in a background was prevented. Furthermore, in Example 2 in which 30 µl of the sample solutions were supplied after the supply of the developing solution, the reflectances were smaller than those in Comparative Example 2 in which the developing solution was supplied after the supply of the same amount of the sample solutions. This indicates that the increase in a background was prevented. Moreover, in Examples 1 and 2, the increase in a background caused by increasing the amount of the samples was prevented. In contrast, in Comparative Examples 1 and 2, background increased markedly by increasing the amount of the samples.

INDUSTRIAL APPLICABILITY

The present invention can be used suitably in the detection (quantitative analysis, semi-quantitative analysis, qualitative analysis, or the like) of a specific substance contained in whole blood, serum, plasma, saliva, urine, spinal fluid, or the like, for example. The present invention is applicable to fields such as clinical tests, biochemical tests, and medical research. The use of the present invention is not limited, and the present invention can be applied to a wide range of fields.

EXPLANATION OF REFERENCE NUMERALS 10, 20, 30, 40, 50, 60: sample analysis tool
11, 21, 41, 51, 61: development member
12, 42, 62: developing solution supply portion
13, 43a, 43b, 43c, 43d, 63: sample supply portion
14, 44, 44a, 44b, 44c, 44d, 64: detection portion
15, 65: enzyme-labeled antibody
16, 66: antigen
17, 67: immobilized antibody
18, 68: complex
19, 69: enzyme
22: developing solution receiving pad
23: waste liquid absorbing pad
24: support
31: case
32: developing solution supply port
33: sample supply port
34: window
a, b, c, d, e, f, g, h: arrow

The invention claimed is:

1. A method for analyzing a sample containing an analyte using a sample analysis tool, the sample analysis tool comprising a development member comprising a buffer solution supply portion, a sample supply portion, and a detection portion provided in this order from upstream to downstream along a flow of a buffer solution, wherein a substance that specifically binds to the analyte in a sample is immobilized in the detection portion, the analysis method comprising:

supplying a sample solution containing the sample to the sample supply portion;

supplying a buffer solution to the buffer solution supply portion prior to the supply of the sample solution such that the sample solution is supplied while the flow of the buffer solution from the buffer solution supply portion toward the sample supply portion is generated through the sample supply portion; and analyzing the analyte by detecting a label in a complex, wherein the sample solution is introduced to the detection portion by the flow of the buffer solution in the development member in the presence of a labeled substance that specifically binds to the analyte, and said labeled substance that specifically binds to the analyte is contained in the sample solution or is disposed in the developing member, and wherein the complex comprising the immobilized substance that specifically binds to the analyte, the analyte, and the labeled substance is formed in the detection portion.

2. The method according to claim 1, wherein the sample analysis tool comprises:

a plurality of the sample supply portions and a plurality of the detection portions, wherein the plurality of the sample supply portions and the plurality of the detection portions are provided for one developing solution supply portion.

3. The method according to claim 1, wherein the sample analysis tool further comprises a case comprising a buffer solution supply port and a sample supply port, and the development member is disposed in the case.

4. The method according to claim 1, wherein the sample analysis tool further comprises a first buffer solution receiving pad disposed to be in contact with an upstream side of the development member, and wherein the supplying of the buffer solution to the buffer solution supply portion comprises supplying the buffer solution to the buffer solution supply portion via the first buffer solution receiving pad such that the buffer solution proceeds to the buffer solution supply portion via the first developing solution receiving pad.

5. The method according to claim 1, wherein the sample analysis tool further comprises a second buffer solution receiving pad disposed to be in contact with a downstream side of the development member with respect to the detection portion.

6. The method according to claim 1, wherein the immobilized substance that specifically binds to the analyte and the labeled substance that specifically binds to the analyte each are an antigen or an antibody.

* * * * *